United States Patent [19]

Haas

[11] 3,940,476
[45] Feb. 24, 1976

[54] ORAL PREPARATIONS FOR PREVENTING DENTAL PLAQUE

[75] Inventor: Gerhard J. Haas, Woodcliff Lake, N.J.

[73] Assignee: General Foods Corporation, White Plains, N.Y.

[22] Filed: Sept. 24, 1973

[21] Appl. No.: 399,879

Related U.S. Application Data

[63] Continuation-in-part of Ser. No. 239,796, March 20, 1972, abandoned, which is a continuation-in-part of Ser. No. 148,203, May 28, 1971.

[52] U.S. Cl. .................................................. 424/49
[51] Int. Cl.² .......................................... A61K 7/16
[58] Field of Search ................................ 424/49–58

[56] References Cited
UNITED STATES PATENTS
1,943,467    1/1934    Bley ....................................... 424/50

OTHER PUBLICATIONS
Chemical Abstracts, Vol. 74, entry 45539b, 1971.

Weuffen et al., *Die Pharmazie*, Vol. 22, pp. 506–510, 1967.

*Accepted Dental Therapeutics*, 35th ed., published by the American Dental Assoc., Chicago, 1973, pp. 255–257.

Primary Examiner—Richard L. Huff
Attorney, Agent, or Firm—Richard Kornutik; Daniel J. Donovan; Thaddius J. Carvis

[57] ABSTRACT

This invention relates to a method inhibiting the formation of dental plaque. This invention has identified a number of compounds (e.g. allyl isothiocyanate, uranine, obtusastyrene, citral, citronellol, nerol and geraniol) which are effective as antimicrobial agents against cariogenic streptococci and which when topically applied to the teeth would be effective for use in oral preparations as a means to reduce dental plaque.

1 Claim, No Drawings

ORAL PREPARATIONS FOR PREVENTING DENTAL PLAQUE

This application is a continuation-in-part of my copending U.S. patent application Ser. No. 239,796, filed Mar. 20, 1972, now abandoned which in turn is related to my copending U.S. patent application Ser. No. 148,203, filed May 28, 1971.

The underlying causes of dental caries are multifaceted. One aspect is the microbiological one. In order for caries to develop, infection by microorganisms has to occur.

During recent years it has been found that the organisms most often associated with the formation of multisurface caries are certain salivary streptococci belonging to the strep mutans group. Multi-surface caries is particularly prevalent in children and young adults; the so-called rampant caries belong to this type. The cariogenic organisms appear to have the special capability of developing a high molecular weight, water-insoluble type of dextran from sucrose. This dextran is believed to be a major constituent of the dental plaque normally associated with dental caries.

Various means have been contemplated for controlling the amount of plaque in the mouth. The use of certain enzymes such as Pancreatin is disclosed in U.S. Pat. No. 3,235,460 as effective to inhibit the formation of dental plaque. Commonlyassigned U.S. patent application, Ser. No. 126,465, filed Mar. 15, 1971 discloses several surface active agents which are also effective to inhibit or reduce the formation of dental plaque.

It has also been proposed to employ direct bactericidal action on the cariogenic microorganisms to assist in the reduction or prevention of dental caries. U.S. Pat. Nos. 2,921,886 and 3,450,812 respectively disclose alkyl morpholine compounds and nitrogen based compounds having an empirical formula of $C_{38}H_{61}NO_{14}$ as antimicrobials which are effective as anticaries agents.

This invention has identified a number of compounds, all known to have some antimicrobial properties, which have been found to be antimicrobial against cariogenic streptococci. These compounds have the apparent ability to either inhibit the growth of or destroy selected cariogenic streptococci.

Broadly, the present invention relates to a method for inhibiting the formation of dental plaque, which comprises topically applying to the teeth as an active ingredient an amount of either one or a combination of (a) allyl isothiocyanate, (b) uranine, (c) obtusastyrene, (d) citral, (e) citronellol, (f) nerol, or (g) geraniol, which is effective in inhibiting the formation of dental plaque and/or dental caries. The use of obtusastyrene is preferred due to its high effectiveness.

By the phrase topical application to the teeth it is meant that the active ingredient is brought into direct contact with the teeth and maintained there for a period of time effective to inhibit the growth of cariogenic bacteria, particularly cariogenic streptococci. The direct contact may be achieved by directly swabbing a concentrated solution of the active ingredient onto the teeth or by holding it in the mouth in a more dilute solution taken directly or derived from a carrier. The active ingredients can be present in suitably effective amounts in preparations such as toothpastes, tooth powders, mouth washes, or the like, or they may be employed in preparations such as chewing gum or lozenges to provide longer periods of contact with the teeth.

Coupled with the problem of identifying antimicrobial compounds effective in reducing dental caries is the necessity that the effective substance may be permitted to act on teeth in the mouth. Thus, not only must the substance possess the requisite effectiveness, it must also possess certain requisite supplementary characteristics such as satisfactory properties from the viewpoint of oral toxicity, acute chronic toxicity, non-sensitization, etc.

An important feature of this invention is the use of compounds which have low toxicity and which may be readily incorporated into a variety of oral preparations.

Ingredients which have shown some activity as antimicrobials against cariogenic streptococci but which are not considered part of this invention are citronellal, neral, geranial and cinnamon saigon oil. It is noted that surprisingly the geometric isomers neral and geranial which combined constitute the active component citral are by themselves relatively inactive. Phenol, a known antimicrobial, has been compared with obtusastyrene to demonstrate relative effectiveness.

Such materials as sweeteners, flavoring, coloring or whitening agents, preservatives, alcohols and the like may be readily incorporated into the oral preparations of this invention. Dentifrice formulations should also contain as a major proportion of the solid ingredients water-insoluble abrasives or polishing agents such as calcium carbonate, tricalcium phosphate, bentonite, etc.

In the preparation of tooth powders it is usually sufficient to mechanically blend the various solid ingredients, including effective amounts of the antimicrobial compound and abrasives, into a homogeneous powder.

Mouth washes or rinses prepared in accordance with this invention will usually comprise an effective amount of the antimicrobial compound dissolved in a suitably flavored liquid vehicle such as an aqueous alcoholic vehicle.

The lozenges or troches contemplated by this invention are prepared by mixing particles of the antimicrobial compound with mucilage and natural or artificial sweeteners and flavoring agents. Gelatin and water is also an effective base for these candy-like products. Chewing gum can be prepared by the substitution of a standard gum base for the mucilage. Suitable bulking agents or fillers may be added to any of these edible products.

The oral preparations employed according to this invention may be prepared in accordance with the skill and practice of the prior art. The distinguishing feature of this invention is the inclusion of an effective amount of selected antimicrobial compounds to reduce the incidence of dental plaque. These antimicrobial compounds may be incorporated into the oral preparation either as a substitute for or in addition to other antiplaque agents which have previously been discovered and employed by the prior art.

The antimicrobial compounds or combination of compounds of this invention should be present in the oral preparations in an amount sufficient to produce an effective concentration of the compounds in the mouth. Normally this involves the formation of oral preparations which contain or release the antimicrobial compound in the mouth at a concentration of about 0.005% to 1% by weight; although it will be apparent from a reading of this specification that the obtusastyrene, citral, citronellol, nerol and geraniol will normally be used at the low end of this range, say 0.005% to 0.2% while the allyl isothiocyanate and uranine will normally be used at the high end of the range, say 0.1% to 1%.

EXAMPLE 1

The compounds were tested at various concentrations in a thioglycollate broth medium inoculated with a known amount of cariogenic organisms (FA-1 strain) and were quantitatively compared with control cultures which did not contain the antimicrobial compound. Additional cultures containing equivalent amounts of compounds found to be less effective as antimicrobial against cariogenic streptococci were also investigated; however, these compounds are not considered as part of this invention.

The method of testing consisted of inoculating 5 or 10 ml. portions of the thioglycollate broth having added thereto 5% sucrose by weight, a pinch of calcium carbonate and the antimicrobial compound (except control), usually in an ethanol solution. All tests were conducted at 37°C. Counts were determined by plating suitable subdilutions on Mitis Salivarius Agar (Difco). The results are summarized in the Tables below.

Table 1 inoculum: $7 \times 10^6$ (FA-1;organisms/ml.)

| compound | | concentration (weight %) | count (FA-1 organisms/ml.) 60 min. | 24 hrs. |
|---|---|---|---|---|
| control | (with 5% alcohol) | — | $5 \times 10^6$ | $2 \times 10^7$ |
| allyl isothio-cyanate | " | 0.1 | $5 \times 10^5$ | $8 \times 10^4$ |
| cinnamon saigon oil | " | 0.1 | $5 \times 10^6$ | $5 \times 10^6$ |

Table 2 inoculum: $4 \times 10^5$ (FA-1;organisms/ml.)

| compound | concentration (weight %) | count at 24 hrs. (FA-1 organisms/ml.) |
|---|---|---|
| control | — | $5 \times 10^8$ |
| uranine | 0.1 | $1 \times 10^8$ |
| uranine | 0.3 | $7 \times 10^2$ |
| uranine | 1 | $6 \times 10^2$ |

Table 3 inoculum: $6 \times 10^6$ (FA-1;organisms/ml.)

| compound | | concentration (weight %) | count (FA-1 organisms/ml.) 10 min. | 20 min. |
|---|---|---|---|---|
| control | (with 5% alcohol) | — | $2 \times 10^7$ | $2 \times 10^7$ |
| obtusastyrene | " | 0.005 | $2 \times 10^7$ | $2 \times 10^7$ |
| " | " | 0.01 | $1 \times 10^6$ | $2 \times 10^2$ |
| " | " | 0.025 | $3 \times 10^3$ | $<10^2$ |

Table 4 inoculum: $8 \times 10^7$ (FA-1;organisms/ml.)

| compound | | concentration (weight %) | 30 min. | 60 min. | 24 hrs. |
|---|---|---|---|---|---|
| control | (with 5% alcohol) | — | $1 \times 10^8$ | $9 \times 10^7$ | $6 \times 10^7$ |
| obtusastyrene | " | 0.005 | $4 \times 10^7$ | $2 \times 10^7$ | $1 \times 10^6$ |
| " | " | 0.0075 | 0 | 0 | 0 |

Table 5 inoculum: $2 \times 10^7$ (FA-1;organisms/ml.)

| compound | | concentration (weight %) | count 10 min. | 20 min. |
|---|---|---|---|---|
| control | (with 2.5% alcohol) | — | $3 \times 10^7$ | $3 \times 10^7$ |
| obtusastyrene | " | .01 | 0 | 0 |
| phenol | " | 0.1 | 0 | 0 |
| " | " | .01 | $1 \times 10^7$ | $4 \times 10^7$ |

Table 6 inoculum: $6 \times 10^6$ (FA-1;organisms/ml.)

| compound | | concentration (weight %) | count 1 hr. | 24 hrs. |
|---|---|---|---|---|
| control | (with 5% alcohol) | — | $6 \times 10^6$ | $8 \times 10^6$ |
| citral | " | 0.1 | $5 \times 10^5$ | 0 |
| " | " | 0.3 | $7 \times 10^3$ | 0 |
| " | " | 1 | 2 | 0 |

Table 7 inoculum: $3 \times 10^5$ (FA-1;organisms/ml.)

| compound | | concentration (weight %) | count 1 hr. | 24 hrs. |
|---|---|---|---|---|
| control | (with 5% alcohol) | — | $2 \times 10^5$ | $8 \times 10^6$ |

Table 7-continued inoculum: 3×10⁵ (FA-1;organisms/ml.)

| compound | concentration (weight %) | count 1 hr. | 24 hrs. |
|---|---|---|---|
| citral | " | 0.03 | $2\times10^5$ | $4\times10^3$ |
| nerol | " | 0.03 | $2\times10^5$ | $3\times10^3$ |
| geraniol | " | 0.03 | $3\times10^4$ | $3\times10^3$ |
| citronellol | " | 0.03 | $1\times10^4$ | $3\times10^3$ |
| citronellal | " | 0.03 | $5\times10^4$ | $9\times10^6$ |
| neral | " | 0.03 | $2\times10^5$ | $7\times10^7$ |
| geranial | " | 0.03 | $3\times10^5$ | $2\times10^6$ |

EXAMPLE 2

Dextran accumulation by cariogenic strep mutans FA-1 on nichrome wires, and its prevention by obtusastyrene.

A technique has been developed by Jordan and Keyes and others in which cariogenic streptococci deposit dextran on nichrome wires. Usually it takes 10 successive transfers to get a thick coating of dextran. This is what happened in the control wires. The test wires were immersed three times a day for five minutes in obtusastyrene solutions in thioglycolate broth. Results may be seen as below.

| Sample | Wire deposit | Scraped off dextran by anthrone procedure[1] (% absorbance) |
|---|---|---|
| Control | Considerable | 0.41 |
| obtusastyrene 0.005% | Slight | 0.05 |
| obtusastyrene 0.025% | None | 0.03 |

[1]Anthrone Reaction: 2 ml. portions of sample suspensions and controls were placed in the bottom of large test tubes. The tubes were placed in an ice bath and 10 ml of anthrone reagent (0.02% anthrone in 70% $H_2SO_4$) were quickly added to each tube. The tubes were mixed and immersed in boiling water for nine minutes. The tubes were then placed in an ice bath. After 30 minutes, absorption readings were taken on a Bechman DB-G at 625 mµ.

This shows that 0.025% obtusastyrene completely prevented dextran formation in this experiment, even though contact was only 3 × 5 minutes a day simulating use in an oral preparation.

EXAMPLE 3

Effect of obtusastyrene on lactobacilli

Lactobacilli are considered important for caries by some investigators. I investigated the activity of obtusastyrene towards two organisms: *Lactobacillus casei* and *Lactobacillus fermente*.

Thioglycolate broth with 5% sucrose added and $CaCO_3$ for pH control as the medium was used. The inocula for both organisms were approximately $1 \times 10^6$ organisms/ml.

After 1 hour in the test tube with 0.0075% obtusastyrene there were less than 100 *L.casei;* in the experiment with *L.fermenti* 100 survived in the presence of 0.0075% obtusastyrene. After 24 hours the controls had multiplied to $1.5 \times 10^8$ organisms/ml showing that we had viable cultures.

The above Examples and explanations are for the purpose of teaching those skilled in the art how to practice the present invention. Upon reading this disclosure, those skilled in the art will be aware of a number of modifications and variations. It is contemplated that these modifications and variations be included within the scope of the present invention which is defined by the following claims.

What is claimed is:

1. A method for inhibiting the formation of dental plaque, which comprises topically applying to the teeth as an active ingredient an amount of obtusastyrene, which is effective in inhibiting the formation of dental plaque.

* * * * *